US006361745B1

(12) United States Patent
Regan et al.

(10) Patent No.: US 6,361,745 B1
(45) Date of Patent: Mar. 26, 2002

(54) MICROARRAY STORAGE DEVICE FOR USE IN AN AUTOMATED MICROARRAY HANDLING SYSTEM

(75) Inventors: Donald T. Regan, Boxborough; Robert T. Milkowski, Groton; George Gyorke, Jr., Somerville; Paul L. St. Cyr, Middleton; Sean R. Doane, Shrewsbury, all of MA (US)

(73) Assignee: Packard Instrument Company, Inc., Meriden, CT (US)

( * ) Notice: Subject to any disclaimer, the term of this patent is extended or adjusted under 35 U.S.C. 154(b) by 0 days.

(21) Appl. No.: 09/392,118

(22) Filed: Sep. 8, 1999

(51) Int. Cl.[7] .................................................. B01L 9/00
(52) U.S. Cl. ......................... 422/104; 422/99; 422/102; 436/43; 436/47; 436/63
(58) Field of Search ................................ 422/102, 104, 422/99; 436/43, 47, 63; 73/864.91; 211/71.01–85.31; 206/405; 229/100, 200; D3/304; D34/39

(56) References Cited

U.S. PATENT DOCUMENTS

| 4,367,915 A | | 1/1983 | Georges ..................... 350/530 |
| 4,483,927 A | * | 11/1984 | Takekawa .................... 436/43 |
| 5,192,503 A | * | 3/1993 | McGrath et al. .............. 422/57 |
| 5,332,549 A | * | 7/1994 | MacIndoe .................... 422/63 |
| 5,364,592 A | * | 11/1994 | Lewis et al. ................. 422/63 |
| 5,690,892 A | | 11/1997 | Babler et al. ................ 422/63 |

* cited by examiner

Primary Examiner—Jill Warden
Assistant Examiner—Yelena Gakh
(74) Attorney, Agent, or Firm—Cesari and McKenna, LLP

(57) ABSTRACT

A microarray storage device includes a cassette having top, bottom and opposite side walls, the front and rear of the cassette being open. The side walls are formed with a multiplicity of parallel rails spaced along the heights of the walls which define compartments in the cassette for supporting a multiplicity of microarrays one above the other. The depth of the cassette is such that the microarrays supported in the compartments project appreciably from the front and/or rear of the cassette. Integral springs are formed in the side walls of the cassette which press down directly on the side edge margins of the microarrays so as to releasably retain the microarrays in their respective compartments. The cassette is designed to be latched to the elevator platform of an associated microwave handling system and a cover may be releasably engaged over the cassette and its contents so that the cover protects those contents and may function as a tool for inserting the cassette into, and removing it from, the associated handling system.

8 Claims, 3 Drawing Sheets

MICROARRAY STORAGE DEVICE FOR USE IN AN AUTOMATED MICROARRAY HANDLING SYSTEM

This invention relates to the automatic quantitative scanning of microarrays. It relates more particularly to a microarray storage device for use in an automated microarray handling system.

BACKGROUND OF THE INVENTION

Microarrays are arrays of very small samples of purified DNA or protein target material arranged as small spots, usually in the order of 100–200 microns in diameter, on a solid substrate. The spots in the array are exposed to complimentary genetic or protein probe samples derived from cells that have been tagged with fluorescent dyes. The probe material binds selectively to target spots only where complimentary bonding sites occur from a process called hybridization. In other words, probe molecules with a similar sequence to the target will bind or hybridize to the target molecules. Dissimilar probe molecules will not bind to the target molecules and will be washed away in a subsequent rinsing process. By measuring the quantity of bound probe molecules, a researcher can determine the likeness between the probe and the target molecules. This technique is used to measure a variety of biological characteristics including gene expression, genotype and gene sequence.

Hybridization experiments must be conducted in large quantities in order to be generally useful. For example, there are approximately one hundred thousand genes in the human genome, several thousand of which are considered in a typical study. Technologies have been developed to allow massively parallel hybridization experiments to be performed on DNA on a very large number of samples comprising a microarray.

In a typical hybridization experiment, the reference DNA is spotted onto a substrate, typically a glass slide similar to a microscope slide. The DNA is mixed with a liquid buffer to form a solution that is laid down on the substrate in droplets. The surface of the substrate is treated to control the size of the spots resulting from the drops and to chemically bind the DNA to the substrate. When the microarray dries, it is left with an ordered array of reference DNA samples bound to its surface.

Such spotting is accomplished by using an instrument called an arrayer which is a robotic device that can spot forty to a hundred microarrays on a substrate or slide in an automated fashion. Typical spotting times are in the range of eight minutes per slide, the substrates or slides being manually loaded and removed from the arrayer.

The next step in the microarray process is to introduce the fluorescently labeled probe DNA. The DNA is mixed in a buffer solution and placed onto the surface of the microarray. A thin piece of glass is then used to sandwich the probe between it and the substrate or slide which causes the probe DNA to spread across the region of the microarray that contains the target DNA.

Next the target and probe are hybridized by putting the microarray into a humid, thermally controlled environment and baking at temperatures ranging from 40–60° C. for periods ranging from thirty minutes to twelve hours depending on the nature of the experiment. During this stage, target and probe molecules with similar structures bind.

After hybridization, the glass cover is removed and the microarray is rinsed to wash away any probe DNA that did not bind to the target DNA.

Finally, the microarray is imaged. For this, the microarray is manually loaded into an imager or scanner where the probe DNA is illuminated by light which excites the fluors in the probe DNA causing the fluors to fluoresce. The brightness of each specimen or spot in the microarray is a function of the fluor density in that specimen or spot. The fluor density is, in turn, a function of the binding affinity or likeness of the probe molecule to the target molecule for each spot. Therefore, the brightness of each spot can be mapped to the degree of similarity between the probe DNA and the target DNA in that spot or sample. In a typical microarray, up to tens of thousands of experiments can be performed simultaneously on the probe DNA allowing for a detailed characterization of complex molecules.

As can be appreciated, performing the above described microarray process manually is costly and time consuming. A researcher or technician is required to handle each microarray at every step in the process, i.e. spotting, hybridization, washing and imaging. The imaging process is particularly labor intensive because each slide is inserted by hand into the imager for single slide imaging while the user waits to load the next slide. The situation becomes acute for high volume users which process several hundred microarrays a day. They will need to hire several technicians just to keep up with the imaging. Thus, there is a need to reduce the amount of handling required to process microarrays and indeed, to process the microarrays in batches.

Also microarrays are susceptible to damage if they are not stored properly. Everything from dust to light can affect the data that is gleaned from the microarrays. Therefore, there is a need for a way to properly store microarrays so that they are not degraded or damaged over time.

We should mention that there do exist mechanisms for loading microscope slides bearing biomedical samples, such as Pap smears, into microscopes; see e.g., U.S. Pat. Nos. 4,367,915 and 5,690,892.

The former patent describes a system which uses two separate mechanisms for loading slides into, and unloading them from, a cassette or magazine. The magazine is indexed to position each specimen slide for access by a horizontal feed mechanism which transfers the specimen slide onto a microscope stage which has controllable X,Y and Z axes to move the specimen slide into the optical viewing field of the microscope. A duplicate mechanism on the other side of the microscope returns the slide to the magazine.

The latter patent describes a system wherein specimen slides are removed from a magazine or cassette by a shuttle which reaches under each slide and lifts up to engage the slide using a complex motion. The weight of the slide is used to keep it in place on the shuttle mechanism, limiting the acceleration that can be applied and the friction forces that can be overcome when transferring the slide to another mechanism. The slides are then passed to a second mechanism which changes the direction of motion of travel into and out of an associated microscope.

Aside from being designed for use with biomedical samples instead of fluorescent microarrays, those prior loading/unloading mechanisms exhibit a great deal of complexity which results in increased size, decreased reliability and increased cost.

There also exist automated microarray scanning or imaging apparatus which use substrate storage cassettes or magazines. Such apparatus do include mechanisms for holding multiple microarrays. However, they invariably require that each substrate or slide be placed in a metal sub-frame or clip prior to loading it into the storage mechanism or magazine.

Both the substrate and the frame are then moved into the scanning field of the apparatus and subsequently scanned. However, as throughput demands increase for microarray processing, this sub-frame approach becomes limiting because of the added manual labor required to place each microarray into a sub-frame. Further, the user needs to gather multiple sub-frames to process a batch of microarrays. The sub-frames also increase the amount of space required by each microarray in the magazine or cassette placing an upper limit on the number of microarrays that can be stored in a magazine of reasonable size.

Currently there are no microarray magazines or cassettes that can be used both as a common interface for different types of microarray processing equipment and as a storage device for a batch of microarrays allowing a user to queue batches of microarrays in such storage devices and protect them when they are stored.

SUMMARY OF THE INVENTION

Thus, an object of the invention is to provide a microarray storage device for use with an automated microarray handling system which can be used as a common platform microarray storage mechanism during the spotting, hybridizing, washing and scanning steps of a microarray process.

Another object of the invention is to provide a device of this type which is easily transferable between various elements of a microarray processing system.

Yet another object of the invention is to provide a microarray cassette which can function as a storage device or mechanism for a relatively large batch of microarrays.

A further object in the invention is to provide a microarray cassette which requires no sub-frames on the microarrays thereby allowing direct-to-glass handling of the microarrays.

Yet another object of the invention is to provide a microarray storage device which protects the microarrays therein from light and particulate matter.

Another object is to provide a storage device of this type which is relatively easy and inexpensive to manufacture in quantity.

Other objects will, in part, be obvious and will, in part, appear hereinafter.

The invention accordingly comprises the features of construction, combination of elements and arrangement of parts which will be exemplified in the following detailed description, and the scope of the invention will be indicated in the claims.

Briefly, our microarray storage device comprises a generally rectangular cassette having top and bottom walls connected by opposite side walls, the front and rear of the cassette being open. The interior surfaces of the side walls are provided with a multiplicity of parallel rails spaced along the heights of those walls which define compartments for supporting a multiplicity of microarrays so that the microarrays are closely spaced one above the other in the cassette. Preferably, the depth of the cassette is designed so that the microarrays supported in the compartments project appreciably from the front and/or rear of the cassette.

Preferably also, the side walls of the cassette are formed with integral springs which press down on the microarrays supported in the cassette to releasably secure the microarrays within their respective compartments both when the cassette is in use and when it is being transported. As will be seen later, these springs bear directly against the substrates of the microarrays at the side edge margins thereof so that they do not contact experimental spots that are present on the upper surfaces of the substrates.

In use, the cassette may be positioned on the elevator platform of the microarray or loading/unloading handling system for an integrated microarray scanning instrument of the type disclosed in our co-pending application Ser. No. 09/390,013 filed Sep. 3, 1999, entitled MICROARRAY LOADING/UNLOADING SYSTEM, which application is hereby incorporated herein by reference. A latching mechanism to be described later fixes the cassette to that platform. The platform then lowers the cassette into the handling apparatus so that the apparatus feeder mechanism has access to the ends of the microarrays protruding from the cassette to enable the apparatus to transfer, in turn, microarrays from the cassette to the associated scanner or other instrument and vice versa. The projecting ends of the microarrays also enable the user to handle the microarrays without risk of finger contact with the experimental spots present on the substrates.

The microarray storage device preferably also includes a cover which may be engaged over the cassette to protectively enclose the microarrays in the cassette when they are not being processed. Desirably, the cover and the cassette are composed of an opaque material which blocks the ambient light which could photobleach the microarrays stored in the device. Thus, the cover shields the microarrays from light, dust and other particulate matter that could degrade the microarrays.

As will be seen, both the cassette and the cover may be molded of a suitable rigid, impact resistant plastic material. Therefore, the storage device can be made in quantity at relatively low cost.

BRIEF DESCRIPTION OF THE DRAWINGS

For a fuller understanding of the nature and objects of the invention, reference should be made to the following detailed description taken in connection with the accompanying drawings, in which.

DESCRIPTION OF THE PREFERRED EMBODIMENT

Figure 1:
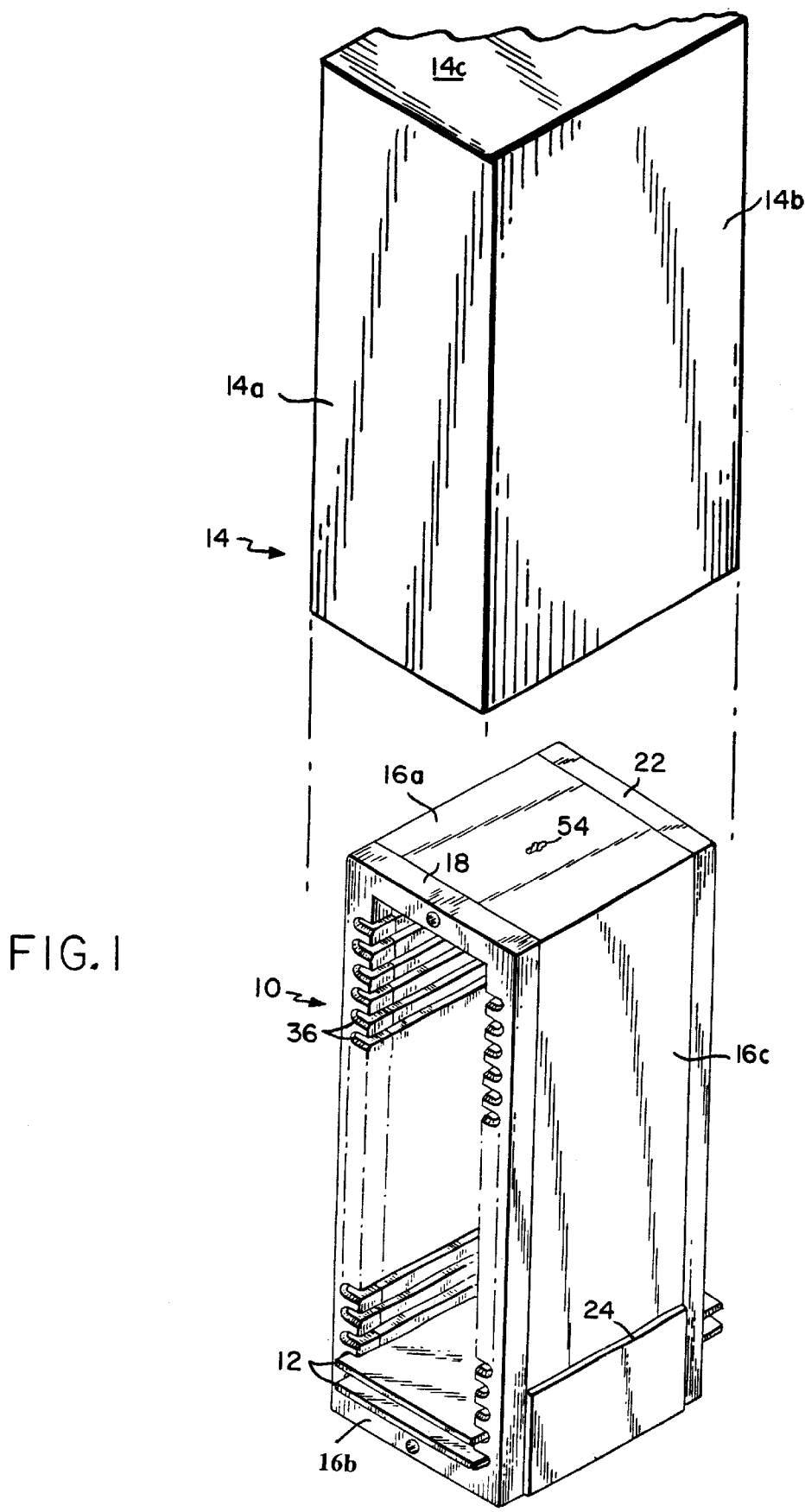
FIG. 1 is an exploded perspective view of a microarray storage device incorporating the invention.

Referring to FIG. 1, our microarray storage device comprises a cassette shown generally at 10 for supporting a multiplicity of vertically spaced microarrays 12, and a cover 14 arranged to engage over cassette 10 and its contents to protectively enclose the microarrays 12 when they are not being processed.

Cassette 10 is a generally rectangular structure having a top wall 16a, a bottom wall 16b and a pair of opposite side wall 16c connecting the top and bottom walls. Preferably, the front and rear edges of cassette 10 are finished off by a pair of front and rear bezels 18 and 22 which define the front and rear openings into cassette.

For reason that will be described later, the cassette side walls 16c are formed with horizontal shoulders 24 near the lower edges of those walls between the bezels 18 and 22, the shoulders 24 projecting slightly beyond the sides of those bezels. As we shall see, the shoulders 24 may be used to retain the cassette 10 in a microarray handling apparatus so that microarrays 12 in the cassette can be processed by an instrument associated with the handling apparatus.

Figure 4:
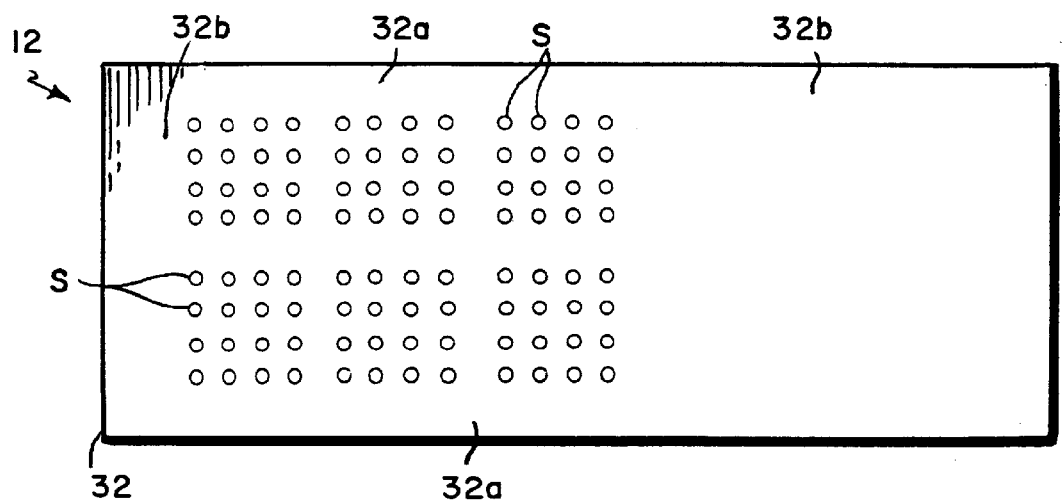
FIG. 4 is a top plan view of a microarray of the type stored in the FIG. 1 storage device.

Refer for a moment to FIG. 4 which shows a microarray 12 in greater detail. It comprises a generally rectangular substrate 32 similar to a microscope slide, e.g., its dimensions are in the order of 1 in.×3 in.×0.04 in. Typically, the substrate is made of soda lime float glass and at least its upper surface is chemically treated to control the size of DNA spots S deposited on substrate 32 and to chemically bind the DNA to the substrate. In the illustrated microarray 12, the spots S are arranged in columns and rows in three arrays more or less centered on the upper surface of the substrate so that relatively wide, e.g., in the order of 1.5 mm. substrate edge margins 32a at both sides of the substrate are free of spots. Even wider, e.g., at least 10 mm, margins 32b are provided at the ends of the substrate.

Figure 2:
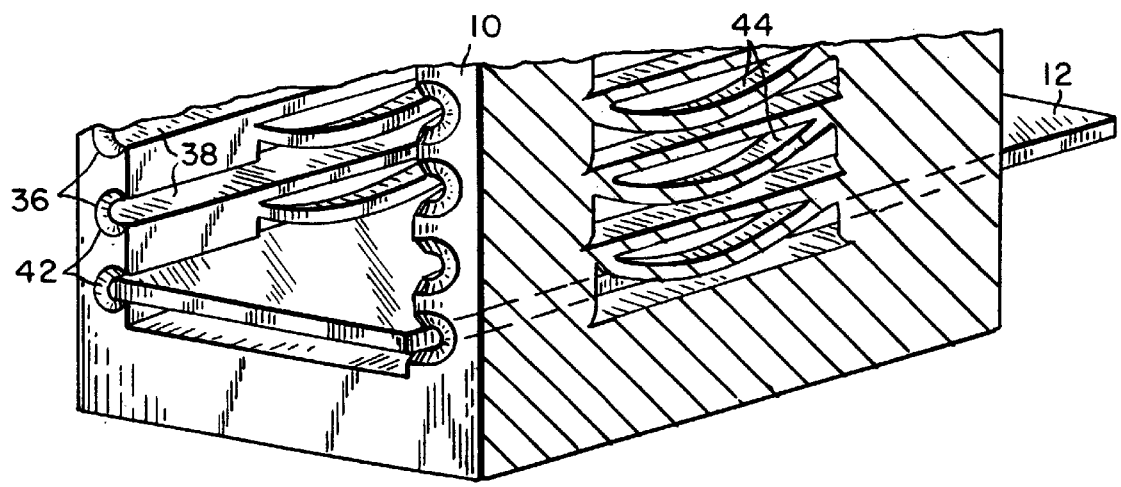
FIG. 2 is a fragmentary perspective view in section showing the interior of the cassette component of the FIG. 1 device in greater detail.

As shown in FIGS. 1 and 2, the side walls of cassette 10 (including those of bezels 18 and 22) are designed to define a series of vertically spaced parallel compartments 36 for releasably supporting a stack of microarrays 12. Preferably, the cassette stacks the microarrays so as to provide a very small spacing, e.g., 0.02 inch, although the spacing may vary depending on the associated handling apparatus. A typical cassette may hold up to twenty microarrays 12 at a pitch tighter than 8/inch.

Figure 3:
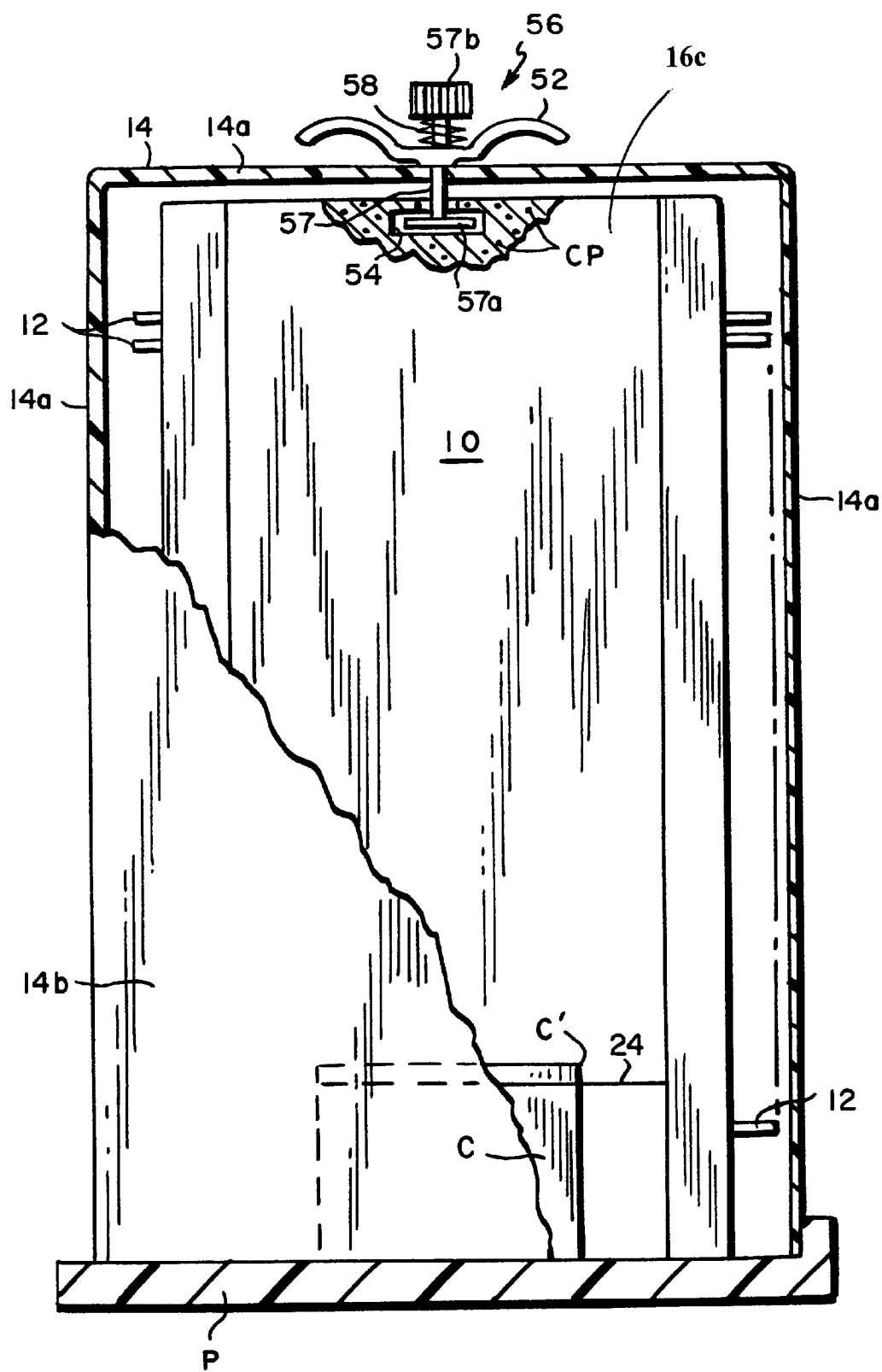
FIG. 3 is a side elevational view with parts broken away of the storage device showing the device's cover installed on the cassette.

As best seen in FIGS. 1 and 3, the front to rear depth of cassette 10 is less than the lengths of the substrates 32 so that when the microarrays are positioned in the cassette as shown, their opposite ends project appreciably, e.g., 10 mm, from the front and rear of the cassette. This permits the automatic feeder of the associated handling apparatus to grasp the ends of the substrates 32 projecting from the rear (or front) of the cassette in order to withdraw them from, or insert them into, the cassette. The other projecting ends may be used for manually handling the microarrays. Preferably only the unspotted end margins 32b of the substrate 32 project from the cassette so that all of the experimental spots S on the substrates remain within the boundaries of cassette 10.

As best seen in FIG. 2, each compartment 36 in cassette 10 is defined by a pair of rails 38 formed at the inner surfaces of the cassette side walls 16c. These rails extend from the front of cassette 10 all the way to the rear thereof. Preferably a recessed notch 42 is formed in the front and rear walls of cassette 10 (i.e., bezels 18 and 22) just above the opposite ends of each rail 38 to introduce, and help guide, the ends of the microarrays 12 onto the rails 38 in the various compartments 36. Each microarray 12 may be slid along the rails 38 in the corresponding compartment 36 until the microarray is more or less centered in the cassette, ie., so that equal lengths of the microarray substrate 32 project from the front and rear of the cassette as shown in FIG. 3.

In order to releasably retain each microarray 12 in the cassette, a pair of downwardly bowed, relatively low force leaf springs 44 are formed integrally in the cassette side walls 16c at the location of each compartment 36. Each pair of leaf springs 44 overlies the corresponding pair of rails 38 and is arranged to bear down on the substrate side edge margins 32a of the microarray 12 positioned on the rails 38 of that compartment. Thus, each microarray is releasably retained in its compartment by frictional forces exerted by the rails 38 and the springs 44 bearing against the opposite surfaces of the substrate side edge margins 32a of the substrate itself midway between the ends of the substrate. Thus, the position of each microarray 12 in its compartment 36 is fixed in all three dimensions by housing side walls 16c, rails 38 and springs 44 without any need for sub-frames. In fact, the illustrated storage device is able to secure each microarray 12 with dimensional tolerances of 76 mm+0.0 mm−1.0 mm in length, 26 mm±0.5 mm in width and 0.09 mm to 1.30 mm in height or thickness.

The bias exerted by the springs 44 on the microarrays in the various compartments 36 is strong enough to prevent the microarrays from moving within their respective compartments during normal handling of cassette 10. However, when a sufficient pulling force is exerted on a projecting end of a microarray by the associated feeder mechanism (or by a user), the microarray may be withdrawn easily from cassette 10 or inserted back into the cassette.

Referring to FIGS. 1 and 3, the other component of the storage device, namely cover 14, may be a simple generally rectangular structure having end walls 14a, side walls 14b a top wall 14c and an open bottom. The cover is sized to fit over a cassette 10 filled with microarrays 12. The cover 14 is dimensioned so that its end walls 14a provide adequate clearance for the projecting ends of the microarrays. Also as shown in FIG. 3 sufficient clearance is provided between the side wall 16c of the cassette and the side walls 14b of the cover so that when the storage device is positioned on the platform P of a microarray handling apparatus such as the one described in the above co-pending application, retaining or latching means extending up from platform P may releasably engage the cassette. Such retaining means are shown here as latches or spring clips C having noses C which can resiliently engage the shoulders 24 at the opposite sides of the cassette as shown in FIG. 3. Of course, other latching means are possible; see the above co-pending application.

Desirably also, the handling apparatus has sufficient space around the platform P to provide clearance for cover 14.

To facilitate lowering cover 14 on and removing it from cassette 10, a handle 52 may be provided at the cover top wall 14c as shown in FIG. 3. Also, means may be included for releasably locking or latching cover 14 to cassette 10. In the illustrated embodiment, the locking means comprise a keyhole 54 formed in the top wall 14a of housing 14 as shown in FIGS. 1 and 3. Keyhole 54 is designed to receive a spring-loaded key 56 mounted to the cover top wall 14c at the handle 52 thereof. Key 56 may comprise a shaft 57 whose inner end 57a is formed as a T and whose outer end is formed as a button 57b. A spring 58 is compressed between button 57b and handle 52 so that the shaft 57 is biased upwardly.

When cover 14 is placed on cassette 10 as shown in FIG. 3 with shaft end 57a aligned with keyhole 54, key 56 may be pushed down into the keyhole. By turning button 57b approximately 90°, key 56 will become locked to the cassette. With the cover locked in place, a technician or other person, using handle 52, may properly position the storage device on the platform P of the associated handling apparatus so that the clips C latch onto shoulders 24 of cassette 10. Then, following rotation of the button 57b to its unlocked position, cover 14 may be removed from the cassette and withdrawn from the apparatus.

Similarly, when it is time to remove cassette 10 from the microarray handling apparatus following completion of a microarray process, the technician may lower cover 14 into the apparatus so that the cover engages over cassette 10. After the cover is secured to the cassette using lock 56, the technician may exert sufficient upward force on handle 52 to retract the housing shoulders 24 from spring clips C so that the entire storage device can be removed from the handling apparatus.

A wide variety of other locking mechanisms may be used to secure cover 14 to cassette 10. For example, a conventional push-detent type of latch may be employed. The objective is to be able to lower cover 14 onto cassette 10 and releasably latch the cover to the cassette so that the cover can be used as a tool to insert a cassette into and withdraw it from the associated handling apparatus. In this way, the microarrays 12 in the cassette are protected by the storage device unless they are actually in the handling apparatus.

As noted above, cassette 10 and its cover 14 are made of an opaque plastic material so that any microarrays contained within the storage device are not affected by ambient light. Preferably also, cassette 10 (and perhaps cover 14 also) is formed of a conductive plastic as indicated by the conductive particles CP in FIG. 3. This prevents prevents the buildup of any static charge that could adversely affect electronic components present in the handling apparatus or other apparatus in which the cassette is installed or with which it is used.

It is apparent from the forgoing that the our microarray storage device greatly reduces the handling required for microarrays, thus reducing labor costs and data microarray degradation and offers a convenient way to sort and safely store microarrays in batches and to introduce the microarrays into and withdraw them from processing apparatus having a common feeder platform.

It will thus be seen that the objects set forth above, among those made apparent from preceding description, are efficiently attained. Also, certain changes may be made in the above construction without departing from the scope of the invention. For example, our storage device may be used to store other small plate-like articles such as microscope slides and the like. Also, the storage device may include an opaque base for cover 14 that fits under cassette 10 so that the cassette and its contents may be fully enclosed and protected. Therefore, it is intended that all matter contained in the above description or shown in the accompanying drawings shall be interpreted as illustrative and not in a limiting sense.

It is also to be understood that the following claims are intended to cover all of the generic and specific features of the invention described herein.

What is claimed is:

1. A microarray storage device for plate-like articles such as microarrays and slides comprising
    a generally rectangular molded plastic cassette having top, bottom and opposite side walls connecting the top and bottom walls and at least one opening into the cassette between said walls;
    pairs of rails molded integrally with the side walls of the cassette, said rail pairs defining a series of aligned, closely spaced, parallel compartments in said cassette, said compartments being accessible through said opening so that a microarray may be inserted into each of said compartments through said opening
    pairs of leaf springs molded integrally with the side walls of the cassette at each compartment, each pair of springs overlying the corresponding pair of rails at that compartment and each spring having opposite ends connected to the corresponding side wall and a portion between said ends which is bowed so that it will bear against a microarray supported by the rails of that compartment, and
    means on at least one of the cassette walls to enable the cassette to be latched to the elevator platform of a microarray handling system.

2. A microarray storage device comprising
    a generally rectangular cassette having top, bottom and opposite side walls connecting the top and bottom walls and at least one opening into the cassette between said walls, said cassette being of an electrically conductive material;
    means on said side walls defining a series of aligned, closely spaced, parallel compartments in said cassette, said compartments being accessible through said opening so that a microarray may be inserted into each of said compartments through said opening, and
    resilient retaining means in each compartment for releasably retaining a microarray in each compartment by direct engagement with the microarray.

3. A microarray storage device comprising
    a generally rectangular cassette having top, bottom and opposite side walls connecting the top and bottom walls and at least one opening into the cassette between said walls;
    means on said side walls defining a series of aligned, closely spaced, parallel compartments in said cassette, said compartments being accessible through said opening so that a microarray may be inserted into each of said compartments through said opening,
    resilient retaining means in each compartment for releasably retaining a microarray in each compartment by direct engagement with the microarray, and
    means on at least one of the cassette walls to enable the cassette to be latched to the elevator platform of a microarray handling system.

4. The storage device defined in claim 3 wherein the cassette is of an opaque material.

5. A microarray storage device comprising
    a generally rectangular cassette having top, bottom and opposite side walls connecting the top and bottom walls and at least one opening into the cassette between said walls;
    means on said side walls defining a series of aligned, closely spaced, parallel compartments in said cassette, said compartments being accessible through said opening so that a microarray may be inserted into each of said compartments through said opening;
    resilient retaining means in each compartment for releasably retaining a microarray in each compartment by direct engagement with the microarray, and
    a generally rectangular cover having a top wall and another wall and being dimensioned to fit over the top and side walls of the cassette so that the cover extends down to the bottom wall of the cassette and said cover other wall is spaced opposite the cassette opening at a distance and covers said opening.

6. The storage device defined in claim 5 and further including interfitting means on the cassette and cover for releasably latching the cover to the cassette.

7. The storage device defined in claim 6 and further including a handle mounted to the cassette cover wall.

8. The storage device defined in claim 5 wherein said cover is of an opaque material.

* * * * *